United States Patent
Tang et al.

[11] 3,983,507
[45] Sept. 28, 1976

[54] TUNABLE LASER SYSTEMS AND METHOD

[75] Inventors: Chung-Liang Tang; John M. Telle, both of Ithaca, N.Y.

[73] Assignee: Research Corporation, New York, N.Y.

[22] Filed: Jan. 13, 1975

[21] Appl. No.: 540,435

Related U.S. Application Data

[63] Continuation-in-part of Ser. No. 538,585, Jan. 6, 1975, abandoned.

[52] U.S. Cl. ........................... 331/94.5 M; 350/157; 331/94.5 C; 350/158
[51] Int. Cl.² ............................................ H01S 3/10
[58] Field of Search ........................... 350/157, 158; 331/94.5 C, 94.5 M

[56] References Cited
UNITED STATES PATENTS
3,868,592  2/1975  Yarborough et al. ........... 331/94.5 C

OTHER PUBLICATIONS

Lopasov et al., Optics & Spectroscopy, vol. 28, No. 3, Mar. 1970, pp. 291–292.

Primary Examiner—Robert J. Webster
Attorney, Agent, or Firm—Cooper, Dunham, Clark, Griffin & Moran

[57] ABSTRACT

A tunable laser includes a birefringent tuning crystal placed in the laser cavity. An electrical signal is applied to the tuning crystal to establish an electrical tuning field within the crystal, and a desired laser tuning rate as a function of the applied electrical signal is established by rotating the optic axis of the crystal through a selected small acute angle from the direction of the laser light path through the crystal. The tunable laser is included in tunable laser systems for derivative spectroscopy and transient spectroscopy.

10 Claims, 9 Drawing Figures

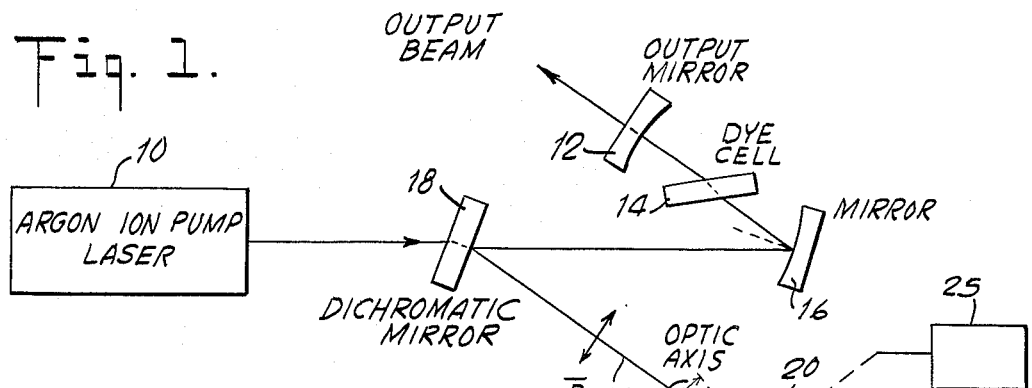
Fig. 1.
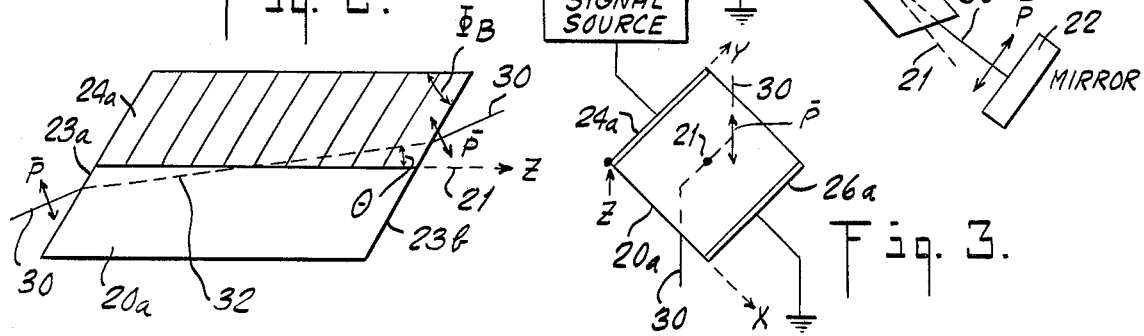
Fig. 2.
Fig. 3.
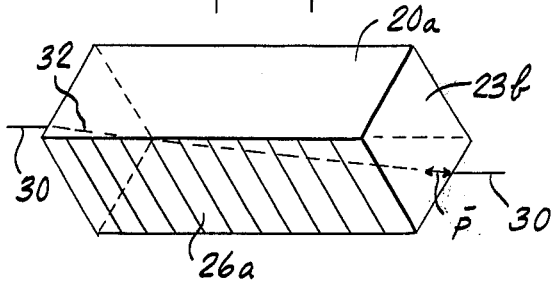
Fig. 4.
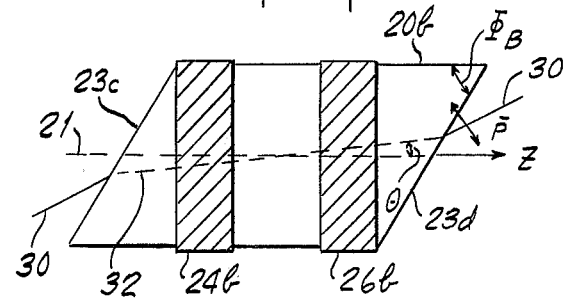
Fig. 5.
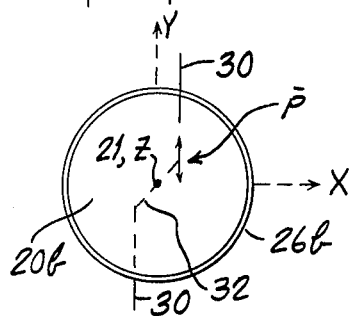
Fig. 7.
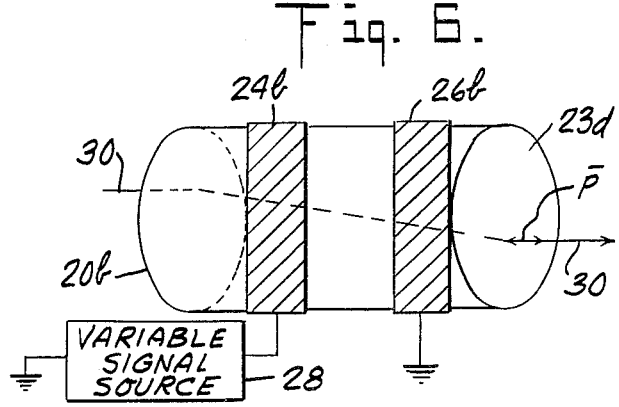
Fig. 6.

TUNABLE LASER SYSTEMS AND METHOD

The United States Government has rights in this invention pursuant to Grant No. GK-33848 awarded by the National Science Foundation.

CROSS REFERENCE

This application is a continuation-in-part of our copending application Ser. No. 538,585, now abandoned, filed Jan. 6, 1975 and entitled TUNABLE LASER AND METHOD.

BACKGROUND OF THE INVENTION

This invention relates to tunable lasers, and more specifically relates to an improved apparatus and method for tuning a laser having a tunable laser cavity.

It is known to employ a birefringent filter as the tuning element in a tunable laser. Tuning of birefringent filter elements has previously been accomplished mechanically as well as electro-optically. One prior art tuning technique utilizes an intracavity grating and a single piece of electro-optical crystal between crossed polarizers. Using this technique, tuning ranges in the order of a few angstroms and tuning rates of a few tenths of an angstrom per kilovolt of applied voltage have been obtained. In order to obtain a larger tuning rate, two suitably oriented crystals with a precisely specified length difference and a stack of Brewster angle plates have been employed. Both of these prior art techniques require the use of a relatively high-gain pulsed laser, and neither technique provides a simple yet precise, sensitive and broadbanded laser tuning device.

U.S. Pat. No. 3,414,839 to Bridges et al discloses a unidirectional ring laser employing a tunable dispersive loss element which is shown in one embodiment as an etalon interposed at nearly normal incidence in the beam path to provide a variation of optical loss for optical transmittance with respect to frequency. A laser modulation device having means for injecting an optical bias by inclining a reflection mirror to create an angular offset between the optical axis of a crystal and the laser optical path is shown in Japanese Patent Publication No. Sho 47/1972-33558, by Goto, published Aug. 25, 1972. Neither of these references shows nor suggests the novel laser tuning apparatus and method disclosed herein.

The lack of a broad-banded laser tuning device which can be simply yet precisely and accurately tuned over a wide range has hampered the development of tunable laser systems for transient and derivative spectroscopy. While the general concept of incorporating a tunable laser light source into a spectroscopy system is known, as illustrated by U.S. Pat. No. 3,588,253 to Wittmann and U.S. Pat. No. 3,805,074 to McCormack, these prior art systems do not offer the unique advantages obtainable with a broad-banded, precisely tunable laser source.

SUMMARY OF THE INVENTION

An object of the invention is to provide a tunable laser which is simple in design and capable of rapid and precise tuning control over a broad tuning range.

It is a further object of the invention to provide a tunable laser having a variable tuning rate and broad tuning range while employing only a single tuning element.

To these and other ends the present invention contemplates a birefringent tuning crystal disposed in the laser light path within the tuning cavity of a tunable laser. The optic axis of the tuning crystal may be positioned at a selected small acute angle to the direction of the laser light path through the crystal to tune the laser to a desired wavelength mechanically.

Alternatively, the optic axis of the crystal may be positioned at a selected angle from the direction of the laser light path to establish a desired tuning rate, and an electrical signal may be applied to the crystal to establish an electrical tuning field within the crystal, to electro-optically tune the laser cavity. The crystal may be fabricated from any material with suitable electro-optic coefficients and transmission characteristics, such as ammonium dihydrogen phosphate (ADP) or deuterated potassium dihydrogen phosphate (KDP). The selectable electrical signal may be applied to the crystal by a pair of electrodes positioned on the crystal surface and connected to an appropriate electrical signal source.

The invention may be employed in conjunction with various crystal-electrode configurations. In one embodiment, a transverse field tuner is formed by placing electrodes on two opposite longitudinal side surfaces of a crystal having a square cross-section normal to the optic axis. Alternatively, a longitudinal field tuner may be constructed by placing annular electrodes around the circumference of a tuning crystal having a circular cross-section normal to the optic axis. In each embodiment, the optic axis of the tuning crystal is rotated through a small selected acute angle from the direction of the laser light path through the crystal to establish the desired laser tuning rate, and the laser is then tuned by applying a selected electrical signal to the electrodes.

Furthermore, the invented tunable laser source may be advantageously incorporated into tunable laser systems for performing transient and derivative spectroscopy. A tunable source suitable for use in a transient spectroscopy system is obtained when a selectable DC voltage is applied to the laser tuning crystal to set the average wavelength of the laser and an AC voltage is applied to repeatedly scan the laser output wavelength through a desired spectrum at a rate determined by the frequency of the AC signal. The limits of the spectrum to be scanned are determined by the amplitude of the AC signal. By passing the tuned laser output through a sample and applying appropriate processing, a desired spectrum centered about a selected wavelength can be repeatedly scanned at a predetermined repetition rate. By electronically modulating the wavelength of the laser light by means of the AC signal and then electrically scanning the laser output across the laser emission band by applying a variable DC signal to the tuning crystal, a tunable laser light source suitable for use in a derivative spectroscopy system is obtained. When the modulated, scanned laser output is transmitted through a sample and suitably processed, a signal proportional to the derivative of the absorption coefficient of the sample with respect to wavelength is obtained.

BRIEF DESCRIPTION OF THE DRAWINGS

FIG. 1 is a block diagram of a tunable laser having a tuning apparatus in accordance with the invention;

FIG. 2 is a top view of a transverse field tuning crystal suitable for use in the tuning apparatus of FIG. 1;

FIG. 3 is a right side view of the tuning crystal of FIG. 2;

FIG. 4 is a front view of the tuning crystal of FIG. 2;

FIG. 5 is a top view of a longitudinal field tuning crystal suitable for use in the tuning apparatus of FIG. 1;

FIG. 6 is a front view of the tuning crystal of FIG. 5;

FIG. 7 is a right side view of the tuning crystal of FIG. 5;

DETAILED DESCRIPTION

Figure 8:
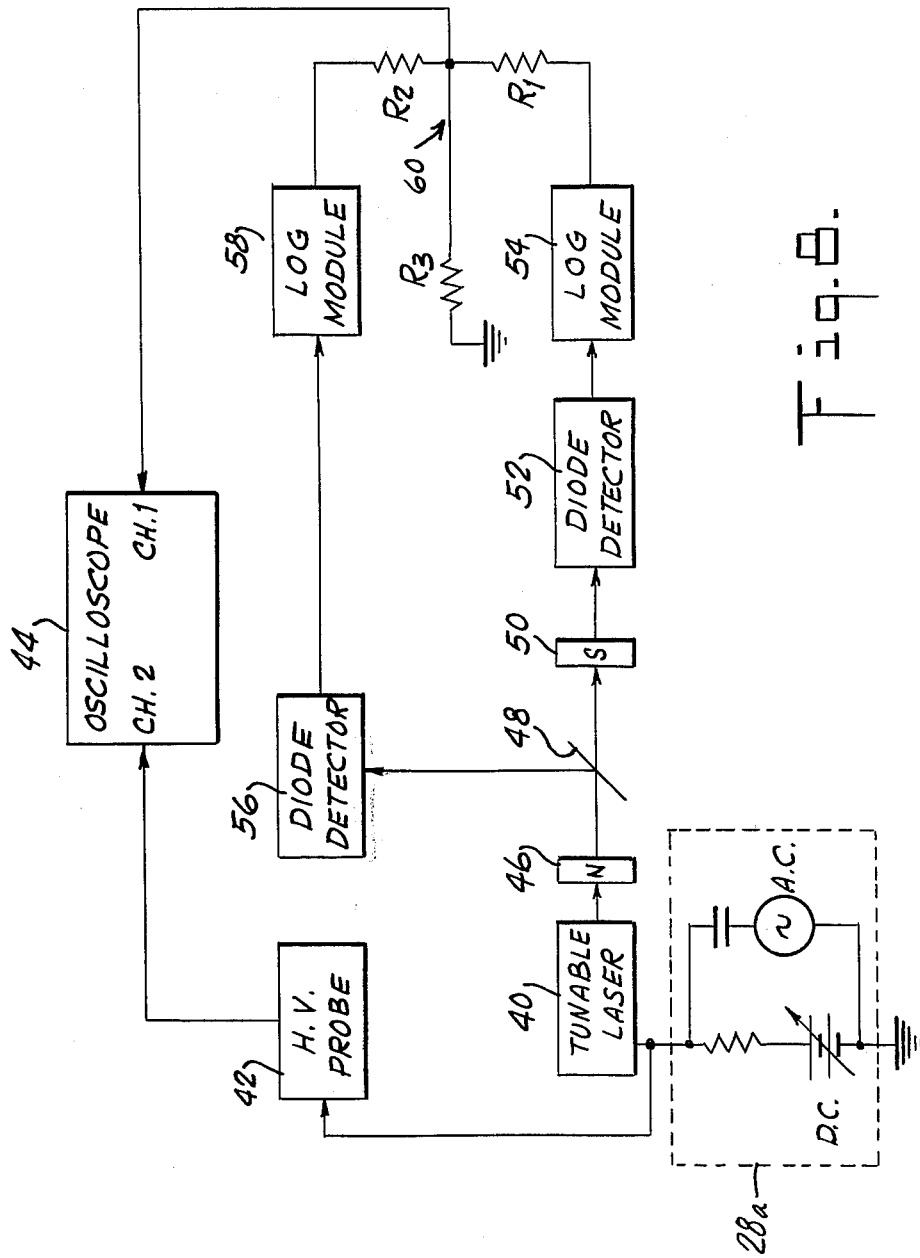
FIG. 8 is a block diagram of a tunable laser transient spectroscopy system.

A tunable continuous-wave dye laser incorporating the invented tuning apparatus is shown in the block diagram of FIG. 1. FIG. 1 is a top view, in simplified block form, of a tunable dye laser, including a laser light source 10, a folded cavity comprising mirrors 12, 16, 18 and 22, and a dye cell 14 and a tuning crystal 20 within the cavity.

Laser light source 10 is a relatively low-power laser, shown in FIG. 1 as an argon ion pump laser. The laser output enters the folded cavity through dichromatic mirror 18, which has an infinite radius of curvature. The laser light is then reflected off mirror 16, which has a 10 centimeter radius of curvature, and enters dye cell 14, where it is almost completely absorbed. Output mirror 12, at one end of the cavity, has a radius of curvature of 5 centimeters and couples out about 5% of the internal cavity power. The dye laser mode is established by mirrors 12, 16 and 18 in conjunction with mirror 22 located at a second end of the cavity. Tuning crystal 20 is located in the laser light path between dichromatic mirror 18 and mirror 22.

Dye cell 14 is of conventional design, and may be of the type having window material of sapphire, Corning cover glass or Spectrosil. The folded cavity arrangement shown in FIG. 1 is an illustrative application of the disclosed tuning apparatus, which may be similarly employed in any tunable laser cavity which has a polarized output due to an internal cavity effect.

Tuning crystal 20 is a birefringent crystal of suitable electro-optic material, such as ADP or KDP. In FIG. 1, tuning crystal 20, as well as dye cell 14, are oriented within the folded cavity so that for a dye laser mode polarized in the plane of the figure the dye mode suffers a minimum refraction loss at the entrance and exit faces of tuning crystal 20 and dye cell 14. The dye mode in dye cell 14 is similarly polarized in the plane of the figure. Tuning crystal 20 is shown oriented with its optic axis 21 at a small acute angle $\theta$ to the direction of the laser light path inside the crystal. The angle $\theta$ is on the order of 1°, but is enlarged in FIG. 1 for clarity of illustration.

Various crystal-electrode configurations may be employed in conjunction with the tuning apparatus of FIG. 1. A tuning crystal 20a suitable for use in a transverse field tuner is shown in FIGS. 2, 3 and 4. FIG. 2 is a top view of the tuning crystal. Tuning crystal 20a has end surfaces 23a and 23b at the Brewster angle $\phi_B$ as shown in FIG. 2. A pair of flat electrodes 24a and 26a are positioned on opposite longitudinal sides of the tuning crystal, as shown in FIG. 3, and a variable signal source 28 is connected between the electrodes to place a selectable electrical signal across the crystal and thereby establish an electrical tuning field therein. In the particular embodiment of the tuning crystal shown in FIGS. 2, 3 and 4, crystal 20a is an 8 × 8 × 32 millimeter ADP crystal, and variable signal source 28 is a ±8 kilovolt variable source. Crystal 20a is initially oriented in the laser cavity so that the planes of the electrodes are disposed at a 45° angle to the plane of polarization of the laser light when the optic or Z axis of the crystal is aligned with the direction of travel of laser light within the crystal. This electrode orientation is most clearly shown in the right side view of FIG. 3.

In FIGS. 1 through 4, the laser mode is shown entering and leaving the tuning crystal by solid lines 30, which intersect the crystal end surfaces 23a and 23b. The continuation of the laser mode inside the crystal is shown by a dotted line 32 joining these end surface intersections. The arrows labeled $\bar{P}$ associated with the laser mode 30 in each of the figures represent the polarization vector of the laser light. In the transverse field tuner of FIGS. 2, 3 and 4, the polarization vector $\bar{P}$ of the laser, prior to entering and after leaving the tuning crystal, has equal components in the Y-Z plane and along the X axis. Laser mode 32 within the crystal lies parallel to the Y-Z plane and makes a small, but finite, angle $\theta$ with the optic axis, as shown respectively in FIG. 3 and FIG. 2. It should be noted that since the angle $\theta$ is formed parallel to the Y-Z plane, the angle designated $\theta$ in FIG. 1 and FIG. 2 is seen in foreshortened perspective.

When tuning crystal 20a is positioned in the laser cavity with its optic axis precisely along the direction of propogation of the laser light, an electrical signal applied to electrodes 24a and 26a will have no effect on the wavelength of the laser light. However, if the crystal is rotated so that the optic axis is at a selected small angle $\theta$ with respect to the laser mode 32 within the crystal, as measured in the Y-Z plane, laser wavelength will become a very sensitive function of the electrical signal applied to electrodes 24a and 26a. Thus, the tilted-crystal laser can be precisely and rapidly tuned electro-optically by adjusting variable signal source 28 to place a desired electrical signal across electrodes 24a and 26a, thereby creating the desired electrical field in the X direction within the crystal. Since tuning rate is a function of $\theta$, a desired rate may be obtained by establishing a corresponding angular rotation of the crystal. By employing a digital power supply for variable signal source 28, extremely fine tuning and precise resetability can be achieved.

Alternatively, the tilting technique may be employed to mechanically tune the laser cavity. A tuning crystal, such as crystal 20a in FIG. 2, may be disposed in the laser cavity as discussed above, and tuning may be accomplished by mechanically varying the angle $\theta$ without applying any electrical signal. However, this technique requires means for accurately positioning the optic axis of the crystal and therefore does not lend itself to rapid tuning.

A longitudinal field tuning crystal configuration is shown in FIGS. 5, 6 and 7. In this embodiment, a crystal 20b, having Brewster angle end surfaces 23c and 23d, has a circular cross-section. A pair of annular electrodes 24b and 26b are positioned around the circumference of the crystal in spaced relationship to each other. As seen in FIG. 7 the X and Y axes have been reoriented, but the basic tuning operation is the same. The polarization vector of the laser prior to entering and after leaving the tuning crystal has only a Y component and the optic or Z axis of crystal 20b is at a selected small acute angle θ to the laser mode 32 within the crystal in a plane containing the Z axis and oriented 45° to both the X and Y axes. The angle θ is shown in foreshortened perspective in FIG. 5. The longitudinal field tuning crystal 20b may also be tuned either electro-optically or mechanically. Electro-optical tuning is achieved by connecting variable signal source 28 across electrodes 24b and 26b, as shown in FIG. 6, and varying the electrical applied signal to establish the desired electrical field along the Z axis within the crystal. Mechanical tuning may be accomplished, as discussed above, by physically rotating the crystal to a desired angle θ.

Using the 8 × 8 × 32 millimeter ADP crystal mentioned previously, a maximum tuning rate of about 60 angstroms per kilovolt has been achieved with the transverse configuration. With the longitudinal configuration, using a crystal 32 millimeters long, a tuning rate of 120 angstroms per kilovolt was achieved. Furthermore, these crystals have been utilized to tune the dye laser across the 360 angstrom dye laser emission band. Significantly, both the tuning rates and tuning ranges are approximately 100 times greater than those previously obtained using an electro-optical cyrstal of comparable size plus intra-cavity polarizers and a grating dispersing element. Furthermore, these results were obtained using a relatively low-gain, continuous-wave dye laser, whereas previous techniques have employed high-gain pulsed dye lasers. In spite of the extremely broad tuning rate and tuning range obtained, the disclosed apparatus may be rapidly yet precisely tuned by utilizing a digital power supply, and may be precisely reset.

For the transverse configuration, the large tuning rate obtained is somewhat surprising, since for the particular cut and orientation of the type of crystals employed the field-induced birefringence should be very small compared to that for prior art configurations. However, the residual birefringence in the crystal in the instant case is even smaller. Since the tuning rate is proportional to the ratio of the field-induced to the zero-field birefringence, a large tuning rate is obtained with the transverse configuration, using a single crystal of the disclosed orientation and cut, in spite of the small field-induced birefringence. For the longitudinal configuration the unusually large tuning rate is primarily achieved because of the small residual birefringence for values of θ near zero.

A transient spectroscopy system incorporating the disclosed tunable laser is shown in FIG. 8. Tunable laser 40, which may be of the type shown in FIG. 1, is connected to variable signal source 28a. A signal from source 28a is applied to the electrodes of the tuning crystal within the laser cavity, as shown in FIG. 3 and FIG. 6. The output of variable signal source 28a contains both a DC and an AC component, and is generated by connecting an AC source and a DC source in parallel in a conventional manner, as shown in simplified form in FIG. 8. The output from supply 28a is sensed by a high voltage probe 42 and may be monitored on one channel of a dual-channel oscilloscope 44.

The output from tunable laser 40 is passed through a neutral density filter 46 and is then split into two components by beam splitter 48 and passed through a dual-beam detection system. A first component of the beam splitter output is passed through a sample 50 and is then detected by diode detector 52 and processed in log module 54. A second component of the beam splitter output is fed directly to diode detector 56 and the output of this detector is processed in log module 58. The output of log module 54, which is proportional to the logarithm of the intensity of light passing through sample 50, is combined in a summing network 60 with the output of log module 58, which is proportional to the logarithm of the intensity of light unattenuated by the sample 50. The output of this summing network, which is composed of resistors R1, R2 and R3 in a conventional configuration, is fed to another channel of oscilloscope 44. The output of summing network 60 may then be displayed on the oscilloscope 44 as a signal which is proportional to the logarithm of the ratio of intensity in the channels of the dual-beam system, which is in turn proportional to the optical density of the sample, neglecting reflection losses.

Simple and precise selection of the desired parameters of tunable laser 40 is obtained by proper adjustment of the AC and DC components of variable signal source 28a. The average wavelength of the laser is set by adjusting the DC component of source 28a. By using a tunable dye laser, such as that shown in FIG. 1, in conjunction with various dyes, the system has a wide potential range of wavelengths from 4300 angstroms to 9000 angstroms.

The AC or modulating component of variable signal source 28a controls both the scanning range and the scanning rate of the spectroscopy system. The magnitude of the AC component determines the scanning wavelength range of the system and the frequency of the AC component determines the scanning rate. The tuning rate of the system is, of course, also determined by the tuning sensitivity of the tunable crystal. For example, an AC component having a frequency of 50 kHz will result in one complete scan of the spectral range covered by the laser every ten microseconds. For an AC voltage of 5 kilovolts, and a tuning crystal sensitivity of 25 angstroms per kilovolt, an AC component of 5 kilovolts will produce a wavelength range of about 125 angstroms. This range may then be centered about any desired wavelength within the tuning range of tunable laser 40 simply by applying the appropriate DC component to the laser from variable signal source 28a.

If laser intensity were independent of wavelength, it would be possible to directly measure the transmission or absorption of the sample 50 in a single-beam detection system. However, the output intensity of modulated laser 40 is generally a function of wavelength, and therefore the dual-beam detection system is employed to compensate for intensity variations due to changes in wavelength. Accordingly, in the dual-beam detection system, one output of beam splitter 48 is passed through sample 50 before being detected by diode detector 52 and processed in log module 54, and the second component of the output from beam splitter 48 is directly detected by diode detector 56 and is processed in log module 58. The output from log modules 54 and 58 is combined in summing network 60 to yield a signal proportional to the log of the ratio of intensities in the two channels. This signal is also proportional to the optical density of the sample, and any signal component due to variations in laser intensity as a function of wavelength is eliminated.

The tunable laser transient spectroscopy system is thus capable of being rapidly and precisely tuned by electronic means, an advantage which is particularly useful in spectral studies of transient or short-lived phenomena. Furthermore, the higher laser intensity per unit wavelength interval offers an improved signal-to-noise ratio over conventional transient spectroscopic techniques. Finally, by tuning the laser source, the necessity for tuning the detection system, as has been done previously in some cases, is eliminated.

Figure 9:
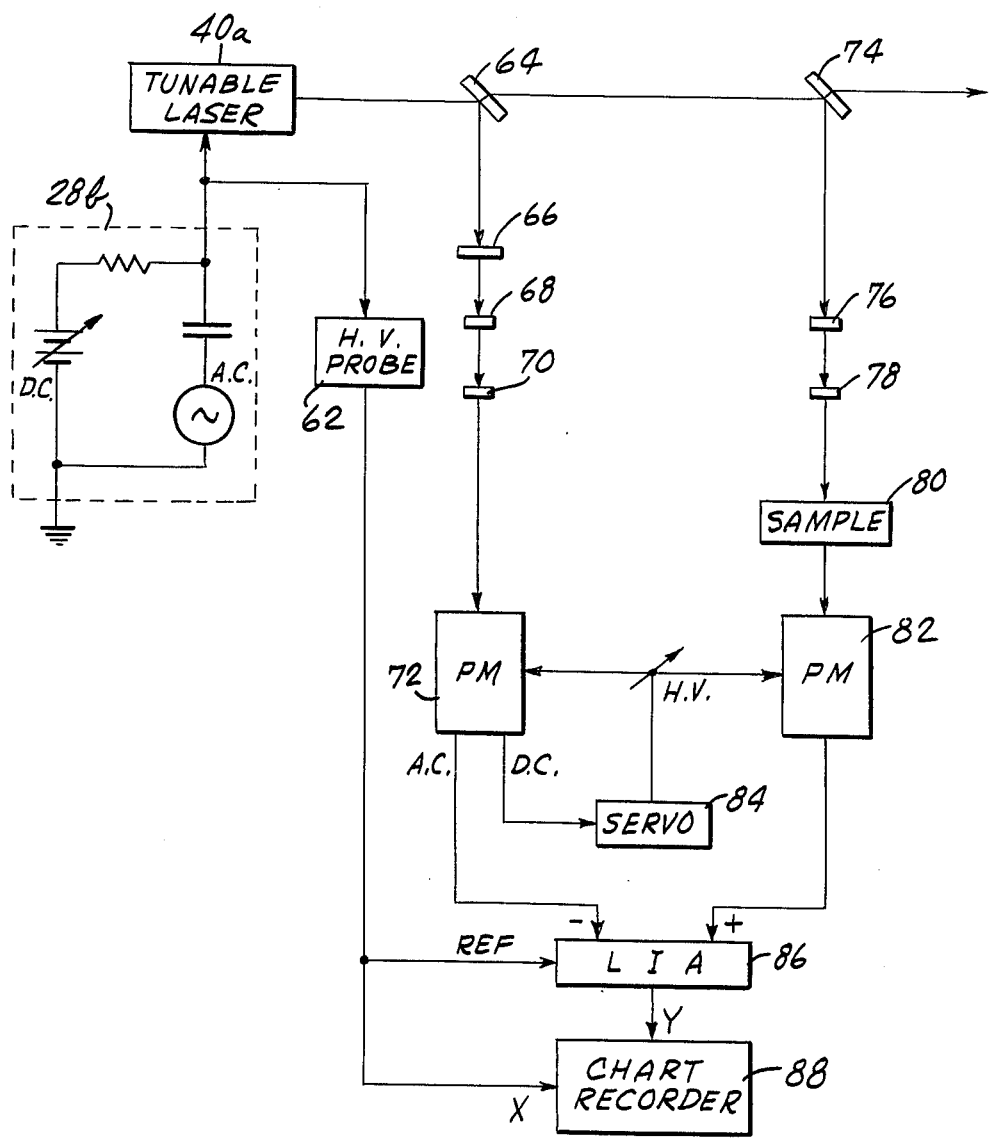
FIG. 9 is a block diagram of a tunable laser derivative spectroscopy system.

A tunable laser derivative spectroscopy system is shown in FIG. 9. A tunable laser 40a, in accordance with the present invention, is connected to variable signal source 28b. A signal from source 28b is applied to the electrodes of a tuning crystal within the laser cavity, in the manner shown in FIG. 3 or FIG. 6. The output of variable signal source 28b contains both a DC and an AC component obtained by connecting an AC source and a DC source in parallel, in a conventional manner, as shown in simplified form in FIG. 9. The output from supply 28b is passed through a high voltage probe 62 and fed to lock-in amplifier 86 and the X input of chart recorder 88.

The output from tunable laser 40a is fed to fused silica optical flats 64 and 74, as shown in FIG. 9, and the reflected components from these optical flats are fed to a dual-beam detection system. The first or reference channel of the dual-beam system comprises fused silica optical flat 66, ground glass 68, ground glass 70 and photomultiplier tube 72. The second or sample channel of the dual-beam detection system comprises ground glass elements 76 and 78, sample 80 and photomultiplier tube 82. Thus, the second or sample channel differs from the first or reference channel in containing sample 80 rather than optical flat 66, but otherwise the two are similar.

In order to compensate for changes in the average light levels reaching the photomultiplier tubes 72 and 82 as a function of variations in laser wavelength, the high voltage on both tubes is automatically adjusted by servo 84 as a function of the average current level of tube 72 to compensate both tubes for any changes in the average light level on tube 72. Alternatively, a separate servo system may be used to control each tube individually.

The outputs from photomultiplier tubes 72 and 82, which result, respectively, from the signals in the reference and sample channels of the dual-beam detection system, are fed to lock-in amplifier 86, which has a differential amplifier input. The output from lock-in amplifier 86 is fed to the Y input of chart recorder 88, while the X input of the chart recorder is derived from variable signal source 28b, as is the reference input to lock-in amplifier 86.

Simple and precise selection of the desired parameters of tunable laser 40a in the derivative spectroscopy system is obtained by proper selection of the AC and DC components of variable signal source 28b. The wavelength of the laser light is electronically modulated by the AC component of source 28b. For example, a 1,000 Hz AC modulating signal having a 100 volt peak-to-peak amplitude would result in a peak-to-peak wavelength excursion of approximately 2.5 angstroms for a tuning crystal sensitivity of 25 angstroms per kilovolt. The average wavelength of the modulated laser signal is then electronically scanned across the laser emission band by automatically scanning the DC component of variable signal source 28b from 0 to 8 kilovolts.

Since the use of a dual-beam system in derivative spectroscopy systems is known, the operation of this system will not be described in detail. Basically, as a result of the wavelength modulation resulting from the AC component of source 28b, an AC amplitude modulation component of the laser light beam is transmitted through the sample, and a signal proportional to the derivative of the absorption coefficient of the sample with respect to wavelength is obtained as the laser is scanned electronically across the laser emission band by the DC component of source 28b. This signal is then measured and processed in lock-in amplifier 86 in a conventional manner, using a signal derived from source 28b as a reference signal, and the resulting output is displayed graphically on chart recorder 88.

The rapid, precise and broad-banded tuning characteristics of the derivative spectroscopy systems containing the tunable laser 40a afford a number of significant advantages. The use of a broad-banded, rapidly tunable laser source, in which both the wavelength modulation and scanning parameters can be precisely adjusted, yields a high resolution, high intensity source which in combination with the other components results in an improved system. The narrower line width of the laser light, combined with precise control of the wavelength modulation, yields a higher resolution than that obtainable in conventional systems. Furthermore, the much higher intensity of the laser light allows materials with a large background absorption to be studied and the well-collimated characteristic of the laser beam permits it to be focused to an extremely small area, thus allowing very small samples to be studied. No means for simply, rapidly and precisely tuning a laser over a broad bandwidth has heretofor been developed, and accordingly prior art laser sources do not afford these significant advantages. It will be seen that the tuning crystal may be varied in position within the laser cavity during operation by a suitable mechanical operator (as shown at 25 in FIG. 1), but ordinarily the crystal will be carefully prepositioned prior to use.

We claim:

1. In a tunable laser having a tunable laser cavity, the improvement which comprises:
   a birefringent tuning crystal disposed in the laser light path within the cavity and having an end surface through which the optic axis of the crystal projects; and
   means for positioning the crystal with said light path incident upon said crystal end surface and the optic axis of the crystal at selected small acute angles to the direction of the laser light path through the crystal, to tune the laser to selected wavelengths.

2. A method for tuning a laser having a tunable laser cavity, which comprises:
   placing a birefringent tuning crystal, having an end surface through which the optic axis of the crystal projects, in the laser light path within the cavity; and
   positioning the crystal with said light path incident upon said crystal end surface and the optic axis of the crystal at selected small acute angles to the direction of the laser light path through the crystal, to tune the laser to selected wavelengths.

3. An apparatus for tuning a laser having a tunable laser cavity, which comprises:
   a birefringent tuning crystal disposed in the laser light path within the cavity and having an end surface through which the optic axis of the crystal projects;
   means for applying a selectable electrical signal to the crystal to establish an electrical tuning field therein; and means for positioning the crystal with said light path incident upon said crystal end surface and the optic axis of the crystal at selected small acute angles to the direction of the laser light path through the crystal, to establish a desired tuning rate at which the laser is tuned by said electrical signal to selected wavelengths.

4. An apparatus as in claim 3 wherein the birefringent tuning crystal comprises an ammonium dihydrogen phosphate crystal.

5. An apparatus as in claim 3 wherein the birefringent tuning crystal comprises a deuterated potassium dihydrogen phosphate crystal.

6. An apparatus as in claim 3, wherein the tuning crystal comprises a crystal having Brewster angle end surfaces, four longitudinal side surfaces parallel to the optic axis of the crystal and a square cross-section normal to the optic axis, and the means for applying an electrical signal to the crystal to establish an electrical tuning field therein comprises a pair of flat electrodes respectively disposed on two opposite longitudinal side surfaces of the crystal parallel to the optic axis, said tuning crystal being rotationally oriented with reference to its optic axis such that the planes of the electrodes would be disposed at a 45° angle to the plane of polarization of the laser light if the optic axis of the crystal were aligned with the direction of the laser light.

7. An apparatus as in claim 3, wherein the tuning crystal comprises a crystal having Brewster angle end surfaces and a circular cross-section normal to the optic axis, and the means for applying an electrical signal to the crystal to establish an electrical tuning field therein comprises a pair of annular electrodes positioned in spaced relationship around the circumference of the crystal and concentric with the optic axis thereof.

8. A method for tuning the wavelength of a laser having a tunable laser cavity, which comprises:
    placing a birefringent tuning crystal, having an end surface through which the optic axis of the crystal projects, in the laser light path within the cavity;
    applying a selectable electrical signal to the crystal to establish an electrical tuning field therein; and
    positioning the crystal with said light path incident upon said crystal end surface and angularly displacing the optic axis of the crystal through selected small acute angles from the direction of the laser light path through the crystal, to produce a desired change in laser wavelength tuning rate as a function of the applied electrical signal to the crystal.

9. An apparatus as in claim 3 wherein the means for applying a selectable electrical signal to the crystal to establish an electrical tuning field therein further comprises:
    an adjustable DC source; and
    an adjustable AC source connected in parallel therewith to form a variable signal source, said variable signal source generating a selectable electrical signal having a DC component which generates an electrical tuning field component to determine the average wavelength of the laser and an AC component which generates an electrical field tuning component to determine the modulation thereof.

10. An apparatus as in claim 3, wherein said selected small acute angles are on the order of one degree.

* * * * *